US006629995B1

(12) United States Patent
Wrenn, Jr. et al.

(10) Patent No.: US 6,629,995 B1
(45) Date of Patent: *Oct. 7, 2003

(54) CAMPTOTHECIN CONJUGATES

(75) Inventors: Simeon M. Wrenn, Jr., Danville, CA (US); Joseph Rubinfeld, Danville, CA (US)

(73) Assignee: Super Gen, Inc., Dublin, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/540,859

(22) Filed: Mar. 31, 2000

(51) Int. Cl.[7] ................................................. A61F 2/06
(52) U.S. Cl. ...................................................... 623/1.42
(58) Field of Search ................................ 623/1.1–1.25, 623/1.35–1.54, 915; 424/435; 514/283, 34, 14, 48; 427/2.24, 2.25

(56) References Cited

U.S. PATENT DOCUMENTS

| | | | | |
|---|---|---|---|---|
| 5,342,348 A | * | 8/1994 | Kaplan | 604/28 |
| 5,468,754 A | * | 11/1995 | Hausheer et al. | 514/283 |
| 5,552,154 A | * | 9/1996 | Giovanella et al. | 424/449 |
| 5,674,192 A | * | 10/1997 | Sahatjian et al. | 604/28 |
| 5,674,874 A | * | 10/1997 | Hausheer et al. | 514/283 |
| 6,057,303 A | * | 5/2000 | Haridas et al. | 514/63 |
| 6,191,119 B1 | * | 2/2001 | Rubinfeld | 514/34 |
| 6,207,832 B1 | * | 3/2001 | Curran et al. | 546/14 |
| 6,291,676 B1 | * | 9/2001 | Burke et al. | 546/48 |
| 6,468,522 B1 | * | 10/2002 | Stein et al. | 424/78.28 |
| 2002/0164374 A1 | * | 11/2002 | Jackson et al. | 424/486 |

FOREIGN PATENT DOCUMENTS

| | | | |
|---|---|---|---|
| WO | WO 99/17804 | 4/1999 | |
| WO | WO 99/17805 | 4/1999 | |
| WO | WO 99/30684 | * 6/1999 | ............ A61K/9/00 |
| WO | WO 01/70275 | 9/2001 | |

OTHER PUBLICATIONS

Hans–Georg Lerchen, XP–000971263, *Camptothecin Antitumor Agents*, 1999, vol. 2. No. 9, pp 896–906.
Charles D. Conover et al., XP–001023467, *Camptothecin Delivery Systems: Enhanced Efficacy And Tumor Accumulation of Camptothecin Following its Conjugation to Polyethylene Glycol Via a Glycine Linker*, Cancer Chemother Pharmacol 1998, pp. 407–414.
Richard B. Greenwald et al., XP–000985272, *Camptothecin–20–PEG Ester Transport Forms: the Effect of Spacer Groups on Antitumor Activity*, 1998, Bioorganic & Medical Chemistry, pp. 551–562.

* cited by examiner

*Primary Examiner*—Michael J. Milano
*Assistant Examiner*—Jackie Tan-Uyen T Ho
(74) *Attorney, Agent, or Firm*—Shirley Chen; Maya Skubatch; Wilson Sonsini Goodrich & Rosati

(57) ABSTRACT

Disclosed is a compound that includes a camptothecin conjugated to a lactone ring protecting moiety. Also disclosed are compositions and kits including the compound, and methods of making and using the compound.

36 Claims, No Drawings

CAMPTOTHECIN CONJUGATES

BACKGROUND OF THE INVENTION

1. Field of the Invention

The present invention relates to improved formulations for the administration of certain camptothecin conjugates.

2. Description of Related Art

20(S)-camptothecin (CPT), a plant alkaloid, was found to have anticancer activity in the late 1950's. Wall, M. et al., *Plant antitumor agents. I. The isolation and structure of camptothecin, a novel alkaloidal leukemia and tumor inhibitor from Camptotheca acuminata*, J. Am. Chem. Soc. 88: 3888–3890, (1966); Monroe E. Wall et al., *Camptothecin: Discovery to Clinic*, 803 Annals of the New York Academy of Sciences 1 (1996). These documents, and all documents (articles, patents, etc.) cited to herein, are incorporated by reference into the specification as if reproduced fully below. The chemical formula of camptothecin was determined to be $C_{20}H_{16}N_2O_4$.

CPT itself is insoluble in water. However, during the sixties and seventies the sodium salt of CPT was derived from CPT through opening of the lactone ring using a mild base. Clinical trials were then conducted using this hydrosoluble, sodium salt derivative of CPT (CPT Na+), which was administered intravenously. The studies were later abandoned because of the high toxicity and low potency of CPT Na+. Gottlieb, J. A., et al., *Preliminary pharmacological and clinical evaluation of camptothecin sodium salt (NSC 100880)*, Cancer Chemother. Rep. 54:461–470 (1979); Muggia, F. M., et al., *Phase I clinical trials of weekly and daily treatment with camptothecin (NSC 100880): Correlation with clinical studies*, Cancer Chemother. Rep. 56:515–521 (1972); Gottlieb, J. A. et al., *Treatment of malignant melanoma with camptothecin (NSC 100880)*, Cancer Chemother. Rep. 56:103–105 (1972); and Moertel, C. G., et al., *Phase II study of camptothecin (NSC 100880) in the treatment of advanced gastrointestinal cancer*, Cancer Chemother Rep. 56:95–101 (1972).

Despite its potential, interest in CPT as a therapeutic remained at a low ebb until the mid-1980's. By that time, drug therapies were being evaluated for treating human cancer using human cancer xenograft lines. During these evaluations, human tumors are serially heterotransplanted into immunodeficient, so-called "nude" mice, and the mice then tested for their responsiveness to a specific drug. (Giovanella, B. C., et al., Cancer 52(7): 1146 (1983)). The data obtained in these studies strongly support the validity of heterotransplanted human tumors into immunodeficient mammals, such as nude mice, as a predictive model for testing the effectiveness of anticancer agents.

CPT, and later some of its substituted forms, elicited differential responses in the cell cycle of nontumorigenic and tumorigenic human cells in vitro. Although it is not yet understood why CPT and some of its substituted forms are cytostatic for nontumorigenic cells and cytotoxic for tumorigenic cells, the selective toxicity of the compounds against tumorigenic cells in vitro and in vivo was an especially interesting feature of these drugs.

Investigators began to experiment with various substituted forms of CPT. Good activity was found when various substitutions were made to the CPT scaffold. For example, 9-Amino-20(S)-Camptothecin (9AC) and 10,11-Methylendioxy-20(S)-Camptothecin (10,11 MD) are capable of having high anticancer activity against human colon cancer xenografts. Giovanella, B. C., et al., *Highly effective topoisomerase-I targeted chemotherapy of human colon cancer in xenografts*, Science 246:1046–1048 (1989).

Additionally, 9-nitrocamptothecin (9NC) has shown high activity against human tumor xenograft models. 9NC has a nine position hydrogen substituted with a nitro moiety. 9NC has inhibited the growth of human tumor xenografts in immunodeficient nude mice and has induced regression of human tumors established as xenografts in nude mice with little or no appearance of any measurable toxicity. D. Chatterjee et al., *Induction of Apoptosis in Malignant and Camptothecin-resistant Human Cells*, 803 Annals of the New York Academy of Sciences 143 (1996).

U.S. Pat. No. 5,552,154 to Giovanella et al. disclosed methods of treating specific forms of cancer with water-insoluble 20(S)-camptothecin and derivatives thereof, having the closed-lactone ring intact. In particular, transdermal, oral and intramuscular methods of administration using solutions of water-insoluble 20(S)-camptothecin were disclosed.

Other substituted CPT compounds that have shown promise include 7-ethyl-10-hydroxy CPT, and other 7, 9, 10, 11-substituted compounds.

However, another problem arose when testing began to be done in an in vivo environment. CPT compounds contain an α-hydroxy-δ-lactone ring functionality that may hydrolyze under physiological conditions. The lactone moiety may open up easily to yield the carboxylate form, particularly in the presence of human serum albumin (HSA), where 97% of 9NC has been observed as converting to the open lactone form. Thomas G. Burke, *Chemistry of the Camptothecins in the Bloodstream: Drug Stabilization and Optimization of Activity*, 803 Annals of the New York Academy of Sciences 29 (1996). As noted above, the biological activity of the closed lactone ring form is far greater than the activity of the open lactone ring, carboxylated form. In addition, some researchers have concluded that a closed lactone ring also may play a role in enhancing passive diffusion of the CPT molecule into cancer cells. Id.

There have been some attempts to overcome the problems associated with opening of the lactone ring. For example, Published PCT Application WO 97/28165 discloses substituted derivatives of camptothecin that are acylated with linear or cyclo alkyl or epoxy moieties at the 20 position hydroxyl moiety. A stated objective of the acylation is to retain the lactone ring and the 20 position hydroxyl group intact. However, the class of molecules disclosed suffers from the problem that the pharmacokinetics of release of the active entity, 9-substituted camptothecin, are suboptimal. No teaching or suggestion is present in the WO 97/28165 Application of how to adjust the pharmacokinetics.

There is therefore a need for a compound, compositions, methods, apparatus, and kits that combine the desirable properties of CPT and its substituted forms with the ability to maintain a closed lactone ring structure.

SUMMARY OF THE INVENTION

The invention is related to compounds comprising a camptothecin conjugated to a lactone ring protecting moiety.

DETAILED DESCRIPTION OF THE INVENTION

In an aspect, the invention is directed to compounds comprising a camptothecin conjugated to a lactone ring protecting moiety. In another aspect, the invention is directed to the compound, wherein the camptothecin is a substituted camptothecin. In another aspect, the invention is directed to the compound, wherein the substituted camptothecin is 9-nitrocamptothecin, 9-aminocamptothecin, 10,11-methylendioxy-20(S)-camptothecin, topotecan, irinotecan, 7-ethyl-10-hydroxy camptothecin, or another substituted camptothecin that is substituted at least one of the 7, 9, 10, 11, or 12 positions. In yet another aspect, the invention is directed to the compound, wherein the substituted camptothecin is 9-nitrocamptothecin, or 9-aminocamptothecin.

In still another aspect, the invention is directed to the compound, wherein the lactone ring protecting moiety is a polyalkylene oxide, dextran, polyvinyl alcohol, carbohydrate polymer, an antibody, streptozoticin or derivatives or mixtures thereof. In an aspect, the invention is directed to the compound, wherein the polyalkylene oxide is a polyethylene glycol. In another aspect, the invention is directed to the compound, wherein the antibody is a monoclonal or polyclonal antibody. In yet another aspect, the invention is directed to the compound, wherein the lactone ring protecting moiety is streptozoticin.

In an aspect, the invention is directed to the compound, wherein a bond connecting the camptothecin and the lactone ring protecting moiety, thus forming the conjugate, is attached to the camptothecin at the 20 position.

In another aspect, the invention is directed to the composition comprising the compound together with a pharmaceutical excipient. In still another aspect, the invention is directed to the composition, wherein the camptothecin is a substituted camptothecin. In another aspect, the invention is directed to the composition, wherein the substituted camptothecin is 9-nitrocamptothecin, 9-aminocamptothecin, 10,11-methylendioxy-20(S)-camptothecin, topotecan, irinotecan, 7-ethyl-10-hydroxy camptothecin, or another substituted camptothecin that is substituted at least one of the 7, 9, 10, 11, or 12 positions. In yet another aspect, the invention is directed to the composition, wherein the substituted camptothecin is 9-nitrocamptothecin, or 9-aminocamptothecin.

In an aspect, the invention is directed to the composition, wherein the lactone ring protecting moiety is a polyalkylene oxide, dextran, polyvinyl alcohol, carbohydrate polymer, an antibody, streptozoticin or derivatives or mixtures thereof. In another aspect, the invention is directed to the composition, wherein the polyalkylene oxide is a polyethylene glycol. In yet another aspect, the invention is directed to the composition, wherein the antibody is a monoclonal or polyclonal antibody. In still another aspect, the invention is directed to the composition, wherein the lactone ring protecting moiety is streptozoticin. In another aspect, the invention is directed to the composition, wherein a bond connecting the camptothecin and the lactone ring protecting moiety, thus forming the conjugate, is attached to the camptothecin at the 20 position.

In an aspect, the invention is directed to kits comprising a container that contains the compound. In another aspect, the invention is directed to the kits, wherein the camptothecin is 9-nitrocamptothecin, or 9-aminocamptothecin. In still another aspect, the invention is directed to the kits, wherein the lactone ring protecting moiety is a polyalkylene oxide, dextran, polyvinyl alcohol, carbohydrate polymer, an antibody, streptozoticin or derivatives or mixtures thereof. In still another aspect, the invention is directed to the kits, wherein the polyalkylene oxide is a polyethylene glycol.

In still another aspect, the invention is directed to kits comprising a container that contains the composition. In still another aspect, the invention is directed to the kits, wherein the camptothecin is 9-nitrocamptothecin, or 9-aminocamptothecin. In another aspect, the invention is directed to the kits, wherein the lactone ring protecting moiety is a polyalkylene oxide, dextran, polyvinyl alcohol, carbohydrate polymer, an antibody, streptozoticin or derivatives or mixtures thereof. In still another aspect, the invention is directed to the kits, wherein the polyalkylene oxide is a polyethylene glycol.

In another aspect, the invention is directed to the implants for administering at least one compound according to the invention, comprising an implant structure and at least one compound according to the invention. In another aspect, the invention is directed to the implants, where the implant comprises a time-release implant. In still another aspect, the invention is directed to the implants, where the implant comprises a gel or polymer implant. In another aspect, the invention is directed to the implants, where the implant is coated and the at least one compound is contained in the coating. In another aspect, the invention is directed to the implants, where the at least one compound according to the invention is contained within the implant structure. In still another aspect, the invention is directed to the implants, wherein the at least one compound is present in an amount effective to reduce cell proliferation once the implant is deployed. In another aspect, the invention is directed to the implants, where the cell proliferation that is reduced is restenotic or cancerous. In yet another aspect, the invention is directed to the implants, where the implant is biodegradable or is formed in situ. In an aspect, the invention is directed to the implants, where the implant comprises a stent.

In an aspect, the invention is directed to methods of treatment comprising inserting an implant into a body wherein the implant comprises the inventive implant. In another aspect, the invention is directed to the methods of using the implants, where the method is used to treat restenosis, various types of cancers, insults to body tissue due to surgery, diseases that produce fibrosis of tissue, repetitive motion disorders, disorders of tissues that are not highly vascularized, and proliferative responses associated with organ transplants. In yet another aspect, the invention is directed to the methods of using the implants, where the method is used to treat coronary, carotid, and cerebral restenotic lesions. In still another aspect, the invention is directed to the methods of using the implants, where the method is used to treat gliomas, other central nervous system tumors, tumors at localized sites including inoperable tumors, tumors where localized treatment of tumors would be beneficial, and solid tumors.

In yet another aspect, the invention is directed to the methods of using the implants, where the method is used to treat cell proliferation associated with joint surgery, bowel surgery, and cheloid scarring. In an aspect, the invention is directed to the methods of using the implants, where the method is used to treat emphysema. In still another aspect, the invention is directed to the methods of using the implants, where the method is used to treat carpal tunnel syndrome. In yet another aspect, the invention is directed to the methods of using the implants, where the method is used to treat disorders of tissues that are not highly vascularized. In another aspect, the invention is directed to the methods of using the implants, where the method is used to treat proliferative responses contributing to potential organ rejections or associated complications. In another aspect, the invention is directed to the method of using the implants, where the method is used to treat proliferative responses occurring as a result of transplantation of the heart, lung, liver, kidney, and other body organs or organ systems.

In an aspect, the invention relates to kits comprising an implant and a mechanism capable of inserting the implant into a body, wherein the implant comprises an implant according to the invention. In another aspect, the invention relates to the kits, wherein the mechanism is an intraluminal catheter. In still another aspect, the invention relates to kits, where the implant comprises a stent.

In yet another aspect, the invention relates to methods of treatment comprising inserting a stent into a body, wherein the stent comprises at least one compound according to the invention. In still another aspect, the invention relates to kits comprising a stent and a mechanism capable of introducing the stent into a body, wherein the stent comprises at least one compound according to the invention. In another aspect, the invention relates to apparatus comprising a container adaptable for connection to an intraluminal catheter, wherein the container contains at least one compound according to the invention.

In still another aspect, the invention relates to methods of treating a cell proliferation disease in a host, comprising administering to the host an amount of the compound according to the invention effective to treat the cell proliferation disease. In yet another aspect, the invention relates to methods of treatment comprising administering at least one compound according to the invention through an intraluminal catheter. In still another aspect, the invention relates to kits comprising a container adaptable for connection to an intraluminal catheter, wherein the container contains at least one compound according to the invention. In another aspect, the invention relates to methods of treatment comprising administering the compound according to the invention in a local fashion.

The inventive compound, compositions comprising the compound, and methods, kits, and apparatus comprising the compound and/or composition will now be described in more detail.

An appropriate place to begin describing the invention is to examine putative mechanisms of action because apprehending such mechanisms helps to put the invention in its proper context. Of course, while such an explanation is helpful, the inventors do not wish to be bound by a particular mechanism of action, because complete understanding of such mechanisms is not necessary to the practice of the invention.

Camptothecin, whether substituted or unsubstituted, is believed to intervene in the mechanism of action of the nuclear enzyme topoisomerase I (topo I), arresting cells in the S phase. It is believed that CPT accomplishes this by stabilizing the covalently linked complexes of DNA-topo I (termed cleavable complexes), thus halting the progression of replication forks. This collision of the replication fork with the cleavable complexes is believed to trigger the apoptotic pathway. Z. Darzynkiewicz et al., *The Cell Cycle Effects of Camptothecin*, 803 Annals of the New York Academy of Sciences 93 (1996). DNA strand breaks are also implicated in the cytotoxic effects of CPT. F. Traganos et al., *Induction of Apoptosis by Camptothecin and Topotecan*, 803 Annals of the New York Academy of Sciences 101 (1996).

The camptothecins according to the invention are conjugated to lactone ring protecting moieties. As discussed above, CPT's activity seems to be diminished for unknown reasons when the lactone ring is opened. HSA, as discussed above, seems to be responsible for, or at least significantly exacerbates the ring opening. Some investigators have hypothesized that this occurs through HSA's shifting of the equilibrium towards the open lactone ring form. Therefore, modifying the camptothecin molecule by conjugating it to the lactone ring protecting moiety so as to prevent the catalytic effects of HSA presumably preserves the in vivo activity of the CPT. This may occur through stearic protection of the lactone ring by the conjugate, thus preventing the enzymatic attachment of HSA to the lactone ring. Other mechanisms also may be at work; knowledge of the exact mechanism is not required to practice this invention.

The lactone ring protecting moiety may be conjugated to the camptothecin at any position on the camptothecin scaffold that retains the camptothecin's activity. In a preferable embodiment, the lactone ring protecting moiety is conjugated to the camptothecin moiety at the camptothecin moiety's 20 position hydroxyl residue.

Additionally, the nature of the lactone ring protecting moiety can improve the performance of the compound in vivo through ways other than simply protecting the lactone ring. For example, there is some evidence that polyalkylene oxide conjugates, especially PEG conjugates, may concentrate in a tumor, because the conjugate will diffuse into the tumor at a greater rate than it will diffuse out of the tumor. See T. L. Cheng et al., *(Poly)ethyelene glycol) Modification of Beta-glucuronidase-Antibody Conjugates for Solid-tumor Therapy by Targeted Activation of Glucuronide Prodrugs*, Cancer Immunol. Immunother. 44:305–15 (1997); S. M. Stribbling et al., *Biodistribution of an Antibody-Enzyme Conjugate for Antibody-Directed Enzyme Prodrug Therapy in Nude Mice Bearing a Human Colon Adenocarcinoma Xenograft*, Cancer Chemother. Pharmacol. 40:277–84 (1997); and K. Kitamura et al., *Polyethylene Glycol Modification of the Monoclonal Antibody A& Enhances its Tumor Localization*, Biochem. Biophys. Res. Commun. 171:1387–94 (1990). Additionally, conjugates may provoke fewer deleterious immune responses as compared to unconjugated materials. See R. B. Pedley et al., *The Potential for Enhanced Tumor Localization by Poly(ethylene glycol) Modification of Anti-CEA Antibody*, Br. J. Cancer 70:1126–30 (1994). Conjugates according to the invention may also have a longer clearance profile than unconjugated materials. See Id. This may be useful when the active entities (camptothecin or lactone ring protecting moieties) of the inventive conjugates produce more therapeutic benefit with longer clearance times. Furthermore, in a preferable embodiment, the lactone ring protecting moiety may be chosen such that it is targeted to a particular cell of interest. For example, when the lactone ring protecting moiety is a tumor antibody, the concentration of CPT in the antigen-bearing tumor locale is greater than if the CPT was unconjugated.

Preferable indications that may be treated using this invention include those involving undesirable or uncontrolled cell proliferation. Such indications include restenosis, various types of cancers such as primary tumors, insults to body tissue due to surgery, diseases that produce fibrosis of tissue, repetitive motion disorders, disorders of tissues that are not highly vascularized, and proliferative responses associated with organ transplants.

Specific types of restenotic lesions that can be treated using the present invention include coronary, carotid, and cerebral lesions. Specific types of cancers that can be treated using this invention include acute myelogenous leukemia, bladder, breast, cervical, cholangiocarcinoma, chronic myelogenous leukemia, colorectal, gastric sarcoma, glioma, leukemia, lung, lymphoma, melanoma, multiple myeloma, osteosarcoma, ovarian, pancreatic, prostrate, stomach, or tumors at localized sites including inoperable tumors or in tumors where localized treatment of tumors would be beneficial, and solid tumors. In a more preferable embodiment, the types of cancer include pancreatic, and/or colorectal. Treatment of cell proliferation due to insults to body tissue during surgery may be possible for a variety of surgical procedures, including joint surgery, bowel surgery, and cheloid scarring. Diseases that produce fibrotic tissue include emphysema. Repetitive motion disorders that may be treated using the present invention include carpal tunnel syndrome. An example of cell proliferative disorders that may be treated using the invention is a bone tumor.

The proliferative responses associated with organ transplantation that may be treated using this invention include those proliferative responses contributing to potential organ rejections or associated complications. Specifically, these proliferative responses may occur during transplantation of the heart, lung, liver, kidney, and other body organs or organ systems.

Camptothecin, when used in the context of this invention, includes both substituted and unsubstituted camptothecins, and analogs thereof. In particular, when substituted camptothecins are used, a large range of substitutions may be made to the camptothecin scaffold, while still retaining activity. In a preferable embodiment, the camptothecin scaffold is substituted at the 7, 9, 10, 11, and/or 12 positions. Such preferable substitutions may serve to provide differential activity over the unsubstituted camptothecin compound. Especially preferable are 9-nitrocamptothecin, 9-aminocamptothecin, 10,11-methylendioxy-20(S)-camptothecin, topotecan, irinotecan, 7-ethyl-10-hydroxy camptothecin, or another substituted camptothecin that is substituted at least one of the 7, 9, 10, 11, or 12 positions.

Native, unsubstituted, camptothecin can be obtained by purification of the natural extract, or may be obtained from the Stehlin Foundation for Cancer Research (Houston, Tex.). Substituted camptothecins can be obtained using methods known in the literature, or can be obtained from commercial suppliers. For example, 9-nitrocamptothecin may be obtained from SuperGen, Inc. (San Ramon, Calif.), and 9-aminocamptothecin may be obtained from Idec Pharmaceuticals (San Diego, Calif.). Camptothecin and various of its analogs may also be obtained from standard fine chemical supply houses, such as Sigma Chemicals.

The CPT-lactone ring protecting moiety conjugates may be prepared by a variety of synthetic approaches. A preferred approach is to react a CPT at the 20-hydroxy moiety with succinic anhydride in pyridine for a period ranging from several hours to days. Upon quenching of the reaction in water or removal of the pyridine followed by extraction, the 20-succinyl ester is removed and purified by recrystallization from an appropriate solvent. The free carboxylic acid of the substituted CPT ester may be coupled to a free amino group (NH2-terminus, epsilon amino group of a lysine, etc.) of a protein (eg, an antibody), peptide (somatostatin for example), polymer or other amine functionality containing drug to produce the amide conjugate. This may be accomplished by use of carbodiimide coupling using morphinol ethyl carbodiimde or N-ethoxycarbonyl-2-ethoxy-1,2-dihydroquinolone. Similar chemistries are known to one of skill, and may be used in the practice of the invention.

In an alternative preferred approach, the reaction may be initiated as above, and then the succinyl ester derivative may be coupled to a free hydroxy to form a diester linkage through the succinic acid group. This may be accomplished by use of carbodiimide coupling or equivalent techniques known to one of skill in the art. Examples of suitable hydroxy groups include, but are not limited to, a carbohydrate group in a glycoprotein such as an antibody, polyethylene glycol, carbohydrates, a serine hydroxy group in a protein, or to the sugar or carbohydrate groups of drugs of interest, such as streptozoticin.

In another preferred synthetic scheme suitable for practice of the invention, the 20 position hydroxy group may be coupled using phosgene or similar entities as a bifunctional coupling reagent. The resulting product can then be used to form phosphate diester derivatives of CPT coupled to various sugars or polyglycol derivatives.

In still another preferred synthetic scheme, an unsaturated fatty acid may be coupled to the 20-hydroxy group of CPT to form an ester by conventional techniques. Next, the unsaturated group may be reacted with meta perchloric benzoic acid, or another epoxide generating reagent. The resulting epoxide then may be coupled with a protein or sugar moiety by acid catalyzed epoxide ring opening and reaction.

Additionally, a number of other bifunctional protein coupling reagents may be used to form the conjugates. Such reagents include, but are not limited to SPDP, bifunctional imidoesters such as dimethyl adipimate-HCl, active esters such as disuccinimidyl suberate, aldehydes such as glutaraldehyde, bis-azido compounds such as bis-(p-azidobenzoyl hexanediamine), and other reactive compounds such as bis-diazonium compounds, diisocyanates, or 1,5-difluoro-2,4-nitrobenzene.

In an alternative preferred embodiment, chemistry similar to that described above could be applied to derivatized CPT to couple the CPT to more than one lactone protecting moiety. For example, the chemistry described above may be used to couple 9AC through the 20-hydroxy group, and the 9-amino group to form a di-substituted camptothecin. Other sorts of equivalent products will occur to one of skill, and are encompassed by the invention.

Conjugated compounds of camptothecins with polyalkylene oxides, dextrans, polyvinyl alcohols, carbohydrate polymers, and derivatives and mixtures thereof are useful in the practice of this invention. Such conjugates can be prepared according to the synthetic methods generally disclosed in U.S. Pat. Nos. 5,219,564 (Zalipsky et al.), 5,605, 976 (Martinez et al.), 5,614,549 (Greenwald et al.), 5,643, 575 (Martinez et al.), and/or U.S. Pat. No. 5,681,567 (Martinez et al.). Preferable conjugates include as the lactone ring protecting moiety: polyethylene glycol (PEG), including mono-, di-, or poly-functional PEG, and monomethyl terminated polyethylene glycol (mPEG).

As noted above, various antibodies are useful as lactone ring protecting moieties in the compounds according to the invention. The antibodies may be conjugated to the CPT in a conventional manner. In a preferable embodiment, the lactone ring protecting moiety is an antibody with affinity to a particular tumor or tumor type. In a more preferable embodiment, the tumor type is a pancreatic or colorectal tumor.

In an alternative preferable embodiment, the lactone ring protecting moiety is an antibody with affinity to a specific target, including such targets as expressed cellular surface receptors, such as adhesion receptors in inflammation pathways; T-cell or T-cell subset receptor pathways.

Antibodies useful in the practice of the invention may either be available commercially, or may be obtained using conventional methods (e.g. Milstein-Köhler). Examples of such antibodies include those disclosed in H. Friess et al., Adjuvant therapy of pancreatic cancer using monoclonal antibodies and immune response modifiers, Int. J. Pancreatol. 21:43–52 (1997); G.D. MacLean et al., Prognostic significance of preimmunotherapy serum CA27.29 (MUC-1) mucin level after active specific immunotherapy of metastatic adenocarcinoma patients, J. Immunother. 20:70–78 (1997); W. Schmiegel, Cytokine-mediated enhancement of epidermal growth factor receptor expression provides an immunological approach to the therapy of pancreatic cancer, Proc. Natl. Acad. Sci. 94:12622–12626 (1997); N. R. Lemoine, Molecular advances in pancreatic cancer, Digestion 58:550–556 (1997); E. Otsuji et al., Application of chimeric Fab fragments of monoclonal antibody A7 for targeting chemotherapy against pancreatic cancer, Gan To Kagaku Ryoho 24:2285–2287 (1997); F. Muller-Pillasch et al., Identification of a new tumor-associated associated antigen TM4SF5 and its expression in human cancer, Gene 208:25–30 (1998); J. Y. Yiannakou et al., Prospective study of CAM 17.1/WGA mucin assay for serological diagnosis of pancreatic cancer, Lancet 349:389–392 (1997); H. Yanagie et al., Inhibition of human pancreatic cancer growth in nude mice by boron neutron capture therapy, Br. J. Cancer 75:660–665 (1997); H. Juhl et al., A monoclonal antibody-cobra venom factor conjugate increases the tumor-specific uptake of a 99mTc-labeled anti-carcinoembryonic antigen antibody by a two-step approach Cancer Res. 55:5749S–5755S (1995); T. Kamagaki et al., Radiolocalization of pancreatic carcinoma xenografts in nude mice with radiolabeled chimeric Fab fragments of anti-carcinoembryonic antigen monoclonal antibody A10, Pancreas 10:258–264 (1995); K. Hirayama et al., Characterization and biodistribution of a mouse/human chimeric antibody directed against pancreatic cancer mucin, Cancer 75:1545–1553 (1995); D. V. Gold et al., Targeting of Xenografted pancreatic cancer with a new monoclonal antibody. PAM4, Cancer Res. 55:1105–1110 (1995); G. J. LaValle et al., Assessment of disseminated pancreatic cancer: a comparison of traditional exploratory laparotomy and radioimmunoguided surgery, Surgery 122:867–871 (1997); B. J. Giantonio et al., Superantigen-based immunotherapy: a phase I trial of PNU-214565, a monoclonal antibody-staphylococcal enterotoxin; A recombinant fusion protein, in advanced pancreatic and colorectal cancer, J. Clin. Oncol. 15:1994–2007 (1997); R. Bei et al., Baculovirus expression of a functional single-chain immunoglobulin and its IL-2 fusion protein, J. Immunol. Methods 186:245–255 (1995).

Other lactone ring protecting moieties may be selected such that they either target the camptothecin moiety to a target of interest, and/or selected such that they have independent pharmaceutical activity. For example, in a preferable embodiment, the lactone ring protecting moiety may comprise streptozoticin. Streptozoticin has been shown to preferentially accumulate in the beta cells of the pancreas, and thus may increase the uptake of the inventive compounds in the pancreas. Additionally, streptozoticin has some pharmacological activity independent from CPT, which may be clinically beneficial in its own right.

In alternative preferable embodiments, cholecystokinin, its analogs and mimics; somatostatin, its analogs and mimics; EGF and its analogs(either pre- or post-treatment with TNFα); Ki-ras oncoprotein and its analogs, and opiod growth factor and its analogs may be useful as the lactone ring protecting moiety.

Additional information regarding these preferable lactone ring protecting moieties may be found throughout the literature, and particularly in I. S. Zagon et al. Opiod growth factor (OGF) inhibits human pancreatic cancer transplanted into nude mice, Cancer Lett. 112:167–175 (1997); C. Militello et al, Clinical evaluation and safety of loxiglumide (CCK-A receptor antagonist) in nonresectable pancreatic cancer patients. Italian Pancreatic Cancer Study Group., Pancreas 14:222–228 (1997); Y. Nio et al., Newly-developing therapies of pancreatic cancer—immunotherapy, gene therapy, differentiation therapy, endocrine therapy and others, Nippon Geka Gakkai Zasshi 98:639–645 (1997); L. Rosenberg, Treatment of pancreatic cancer. Promises and problems of tamoxifen. somatostatin analogs, and gemcitabine, Int. J. Pancreatol. 22:81–93 (1997); R. M. Mohammad et al., Establishment of a human pancreatic tumor xenograft model: potential application for preclinical evaluation of novel therapeutic agents, Pancreas 16:19–25 (1998).

The lactone protecting moieties and other reagents that were used in the syntheses discussed above, but were not obtained by following literature syntheses (such as phosgene, succinic acid, fatty acids, polyethylene glycol, streptozoticin, etc.) may be obtained from a typical reagent supply house, such as Sigma Chemicals.

In a preferred embodiment, the conjugates according to the invention comprise camptothecin conjugated to a lactone ring protecting moiety, with the proviso that unsubstituted or substituted 20(S)-camptothecin conjugated to polyalkylene oxides, such as polyethylene glycol, is excluded. In another preferred embodiment, the conjugates according to the invention comprise camptothecin conjugated to a lactone ring protecting moiety, with the proviso that substituted or unsubstituted 20(S)-camptothecin conjugated to a antibody, such as a monoclonal or polyclonal antibody, is excluded.

The inventive compounds may be administered as compositions that comprise the inventive compounds. Such compositions may include, in addition to the inventive compounds, conventional pharmaceutical excipients, and other conventional, pharmaceutically inactive, agents. Additionally, the compositions may include active agents in addition to the inventive compound. These additional active agents may include additional compounds according to the invention, or one or more other pharmaceutically active agents. In preferable embodiments, the inventive compositions will contain the active agents, including the inventive compound, in an amount effective to treat an indication of interest.

The inventive compounds and/or compositions may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The inventive compounds and compositions may be administered by a variety of routes, and may be administered or coadministered in any conventional dosage form. Coadministration in the context of this invention is defined to mean the administration of more than one therapeutic in the course of a coordinated treatment to achieve an improved clinical outcome. Such coadministration may also be coextensive, that is, occurring during overlapping periods of time.

One therapeutically interesting route of administration or coadministration is local delivery. Local delivery of inhibitory amounts of inventive compounds and/or compositions can be by a variety of techniques and structures that administer the inventive compounds and/or compositions at or near a desired site. Examples of local delivery techniques and structures are not intended to be limiting but rather as illustrative of the techniques and structures available. Examples include local delivery catheters, site specific carriers, implants, direct injection, or direct applications.

Local delivery by a catheter allows the administration of a inventive compounds and/or compositions directly to the desired site. Examples of local delivery using a balloon catheter are described in EP 383 492 A2 and U.S. Pat. No. 4,636,195 to Wolinsky. Additional examples of local, catheter-based techniques and structures are disclosed in U.S. Pat. No. 5,049,132 to Shaffer et al. and U.S. Pat No. 5,286,254 to Shapland et al.

Generally, the catheter must be placed such that the inventive compounds and/or compositions can be delivered at or near the desired site. Dosages delivered through the catheter can vary, according to determinations made by one of skill, but often are in amounts effective to create a cytotoxic or cytostatic effect at the desired site. Preferably, these total amounts are less than the total amounts for systemic administration of the inventive compounds and/or compositions, and are less than the maximum tolerated dose. The inventive compounds and/or compositions delivered through catheters preferably should be formulated to a viscosity that enables delivery through a small treatment catheter, and may be formulated with pharmaceutically acceptable additional ingredients (active and inactive).

Local delivery by an implant describes the placement of a matrix that contains the inventive compounds and/or compositions into the desired site. The implant may be deposited by surgery or other means. The implanted matrix releases the inventive compounds and/or compositions by diffusion, chemical reaction, solvent activators, or other equivalent mechanisms. Examples are set forth in Lange, *Science* 249:1527–1533 (September, 1990). Often the implants may be in a form that releases the inventive compounds and/or compositions over time; these implants are termed time-release implants. The material of construction for the implants will vary according to the nature of the implant and the specific use to which it will be put. For example, biostable implants may have a rigid or semirigid support structure, with inventive compound and/or composition delivery taking place through a coating or a porous support structure. Other implants made be made of a liquid that stiffens after being implanted or may be made of a gel. The amounts of inventive compound and/or composition present in or on the implant may be in an amount effective to treat cell proliferation generally, or a specific proliferation indication, such as the indications discussed herein.

One example of local delivery of the inventive compound and/or composition by an implant is use of a biostable or bioabsorbable plug or patch or similar geometry that can deliver the inventive compound and/or composition once placed in or near the desired site. An example of such implants can be found in U.S. Pat. No. 5,429,634 to Narciso, Jr.

A particular application of use of an implant according to the invention is treatment of cell proliferation in tissue that is not highly vascularized, as discussed briefly above. An example of such tissue is bone tissue. The difficulty in treating uncontrolled proliferative cell growth in bone tissue may be exemplified by the difficulties in treating bone tumors. Such tumors are typically refractory to treatment, in part because bone tissue is not highly vascularized. An implant in or near the proliferative site may potentially have localized cytotoxic or cytostatic effects with regard to the proliferative site. Therefore, in one embodiment, the invention may be used to treat bone tumors.

Another example of local delivery by an implant is the use of a stent. Stents are designed to mechanically prevent the collapse and reocclusion of the coronary arteries. Incorporating an inventive compound and/or composition into the stent may deliver the agent directly to or near the proliferative site. Certain aspects of local delivery by such techniques and structures are described in Kohn, *Pharmaceutical Technology* (October, 1990). Stents may be coated with the inventive compound and/or composition to be delivered. Examples of such techniques and structures may be found in U.S. Pat. Nos. 5,464,650 to Berg et al., 5,545,208 to Wolff et al., 5,649,977 to Campbell, 5,679,400 to Tuch, EP 0 716 836 to Tartaglia et al. Alternatively, the inventive compound and/or composition loaded stent may be biorotable, i.e. designed to dissolve, thus releasing the inventive compound and/or composition in or near the desired site, as disclosed in U.S. Pat. No. 5,527,337 to Stack et al. The present invention can be used with a wide variety of stent configurations, including, but not limited to shape memory alloy stents, expandable stents, and stents formed in situ.

Amounts of the inventive compound and/or composition delivered by the stent can vary, according to determinations made by one of skill, but preferably are in amounts effective to create a cytotoxic or cytostatic effect at the desired site. Preferably, these total amounts are less than the total amounts for systemic administration of the inventive compound and/or composition, and are preferably less than the maximum tolerated dose. Appropriate release times can vary, but preferably should last from about 1 hour to about 6 months, most preferably from about 1 week to about 4 weeks. Formulations including the inventive compound and/or composition for delivery of the agent via the stent can vary, as determinable by one of skill, according to the particular situation, and as generally taught herein.

Another example is a delivery system in which a polymer that contains the inventive compound and/or composition is injected into the target cells in liquid form. The polymer then cures to form the implant in situ. One variation of this technique and structure is described in WO 90/03768 to Donn.

Another example is the delivery of an inventive compound and/or composition by polymeric endoluminal sealing. This technique and structure uses a catheter to apply a polymeric implant to the interior surface of the lumen. The inventive compound and/or composition incorporated into the biodegradable polymer implant is thereby released at the desired site. One example of this technique and structure is described in WO 90/01969 to Schindler.

Another example of local delivery by an implant is by direct injection of vesicles or microparticulates into the desired site. These microparticulates may comprise substances such as proteins, lipids, carbohydrates or synthetic polymers. These microparticulates have the inventive compound and/or composition incorporated throughout the microparticle or over the microparticle as a coating. Examples of delivery systems incorporating microparticulates are described in Lange, *Science,* 249:1527–1533 (September, 1990) and Mathiowitz, et al., *J. App. Poly Sci.* 26:809 (1981).

Local delivery by site specific carriers describes attaching the inventive compound and/or composition to a carrier which will direct the drug to the desired site. Examples of this delivery technique and structure include the use of carriers such as a protein ligand or a monoclonal antibody. Certain aspects of these techniques and structures are described in Lange, Science 249:1527–1533.

Local delivery also includes the use of topical applications. An example of a local delivery by topical application is applying the inventive compound and/or composition directly to an arterial bypass graft during a surgical procedure. Other equivalent examples will no doubt occur to one of skill in the art.

The inventive compounds and/or compositions may be used in the form of kits. The arrangement and construction of such kits is conventionally known to one of skill in the art. Such kits may include containers for containing the inventive compounds and/or compositions, and/or other apparatus for administering the inventive compounds and/or compositions.

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents. Additionally, the following examples are appended for the purpose of illustrating the claimed invention, and should not be construed so as to limit the scope of the claimed invention.

EXAMPLES

Example 1

A supply of 9NC is obtained from SuperGen, Inc. The 9NC is reacted with succinic anhydride in pyridine for two days. The reaction mixture is quenched in water, and is then extracted. Next, the 20-succinyl ester is removed and purified by recrystallization from an appropriate solvent.

An antibody is then obtained according to the methods set forth in E. Otsuji et al., *Application of chimeric Fab fragments of monoclonal antibody A7 for targeting chemotherapy against pancreatic cancer*, Gan To Kagaku Ryoho 24:2285–2287 (1997). The antibody is conjugated to the 20-succinyl ester using morphinol ethyl carbodiimde. The resulting compound is purified using liquid chromatography.

The compound is then tested for activity using the human tumor xenograph models outlined in B. C. Giovanella et al., *Protocols for the Treatment of Human Tumor Xenografts with Camptothecins*, 803 Annals of the New York Academy of Sciences 181 (1996), and Henry S. Friedman et al., *Treatment of Central Nervous System Xenografts with Camptothecins*, 803 Annals of the New York Academy of Sciences 210 (1996).

Example 2

A supply of 9AC is obtained from Stehlin Research Institute. The 9AC is reacted with succinic anhydride in pyridine for two days. The reaction mixture is quenched in water, and is then extracted. Next, the 20-succinyl ester is removed and purified by recrystallization from an appropriate solvent.

An antibody is then obtained according to the methods set forth in D. V. Gold et al., *Targeting of Xenografted pancreatic cancer with a new monoclonal antibody. PAM4*, Cancer Res. 55:1105–1110 (1995). The antibody is conjugated to the 20-succinyl ester using morphinol ethyl carbodiimde. The resulting compound is purified using liquid chromatography.

The compound is then tested for activity using the human tumor xenograph models outlined in B. C. Giovanella et al., *Protocols for the Treatment of Human Tumor Xenografts with Camptothecins*, 803 Annals of the New York Academy of Sciences 181 (1996), and Henry S. Friedman et al., *Treatment of Central Nervous System Xenografts with Camptothecins*, 803 Annals of the New York Academy of Sciences 210 (1996).

Example 3

A supply of 20(S)-camptothecin is obtained by purifying the natural extract. This material is then reacted with phosgene. The resulting product is then purified. An antibody is then obtained according to the methods set forth in B. J. Giantonio et al., *Superantigen-based immunotherapy: a phase I trial of PNU-214565, a monoclonal antibody-staphylococcal enterotoxin; A recombinant fusion protein, in advanced pancreatic and colorectal cancer*, J. Clin. Oncol. 15:1994–2007 (1997). The phosphate diester conjugate is then formed using the antibody and the 9AC phosgene product. The resulting compound is purified using liquid chromatography.

The compound is then tested for activity using the human tumor xenograph models outlined in B. C. Giovanella et al., *Protocols for the Treatment of Human Tumor Xenografts with Camptothecins*, 803 Annals of the New York Academy of Sciences 181 (1996), and Henry S. Friedman et al., *Treatment of Central Nervous System Xenografts with Camptothecins*, 803 Annals of the New York Academy of Sciences 210 (1996).

Example 4

A supply of 10,11-methylendioxy-20(S)-camptothecin is obtained from Sigma Chemicals. The 10,11-methylendioxy-20(S)-camptothecin is reacted with succinic anhydride in pyridine for two days. The reaction mixture is quenched in water, and is then extracted. Next, the 20-succinyl ester is removed and purified by recrystallization from an appropriate solvent.

An antibody is then obtained according to the methods set forth in F. Muller-Pillasch et al., *Identification of a new tumor-associated antigen TM4SF5 and its expression in human cancer*, Gene 208:25–30 (1998). The antibody is conjugated to the 20-succinyl ester using morphinol ethyl carbodiimde. The resulting compound is purified using liquid chromatography.

The compound is then tested for activity using the human tumor xenograph models outlined in B. C. Giovanella et al., *Protocols for the Treatment of Human Tumor Xenografts with Camptothecins*, 803 Annals of the New York Academy of Sciences 181 (1996), and Henry S. Friedman et al., *Treatment of Central Nervous System Xenografts with Camptothecins*, 803 Annals of the New York Academy of Sciences 210 (1996).

Example 5

A supply of 9NC is obtained from SuperGen, Inc. This material is then reacted with phosgene. The resulting product is then purified. A supply of polyethylene glycol, averaging 100,000 molecular weight, is obtained from Sigma Chemical. The PEG phosphate diester conjugate is then formed using the PEG and the 9NC phosgene product. The resulting compound is purified using liquid chromatography.

The compound is then tested for activity using the human tumor xenograph models outlined in B. C. Giovanella et al., *Protocols for the Treatment of Human Tumor Xenografts with Camptothecins,* 803 Annals of the New York Academy of Sciences 181 (1996), and Henry S. Friedman et al., *Treatment of Central Nervous System Xenografts with Camptothecins,* 803 Annals of the New York Academy of Sciences 210 (1996).

Example 6

A supply of 9AC is obtained from the Stehlin Research Institute. Using conventional techniques, oleic acid is coupled to the 20-hydroxy group of the 9AC to form an ester. Next, the unsaturated group of the oleic acid is reacted with meta perchloric benzoic acid to form an epoxide. The resulting epoxide is purified. A supply of polyethylene glycol, averaging 100,000 molecular weight, is obtained. The PEG is then reacted to the 9AC oleic epoxide by acid catalyzed epoxide ring opening to form a product. The resulting compound is purified using liquid chromatography.

The compound is then tested for activity using the human tumor xenograph models outlined in B. C. Giovanella et al., *Protocols for the Treatment of Human Tumor Xenografts with Camptothecins,* 803 Annals of the New York Academy of Sciences 181 (1996), and Henry S. Friedman et al., *Treatment of Central Nervous System Xenografts with Camptothecins,* 803 Annals of the New York Academy of Sciences 210 (1996).

Example 7

A supply of 10,11-methylendioxy-20(S)-camptothecin is obtained from Sigma Chemicals. This is then conjugated to polyethylene glycol, averaging 100,000 molecular weight, according to the methods disclosed in U.S. Pat. No. 5,614,549 (Greenwald et al.). The resulting compound is purified using liquid chromatography.

The compound is then tested for activity using the human tumor xenograph models outlined in B. C. Giovanella et al., *Protocols for the Treatment of Human Tumor Xenografts with Camptothecins,* 803 Annals of the New York Academy of Sciences 181 (1996), and Henry S. Friedman et al., *Treatment of Central Nervous System Xenografts with Camptothecins,* 803 Annals of the New York Academy of Sciences 210 (1996).

Example 8

A supply of 20(S) camptothecin is obtained from Sigma Chemicals. The CPT is reacted with succinic anhydride in pyridine for two days. The reaction mixture is quenched in water, and is then extracted. Next, the 20-succinyl ester is removed and purified by recrystallization from an appropriate solvent.

Somatostatin is then obtained from Sigma Chemicals. The somatostatin is conjugated to the 20-succinyl ester using morphinol ethyl carbodiimde. The resulting compound is purified using liquid chromatography.

The compound is then tested for activity using the human tumor xenograph models outlined in B. C. Giovanella et al., *Protocols for the Treatment of Human Tumor Xenografts with Camptothecins,* 803 Annals of the New York Academy of Sciences 181 (1996), and Henry S. Friedman et al., *Treatment of Central Nervous System Xenografts with Camptothecins,* 803 Annals of the New York Academy of Sciences 210 (1996).

Example 9

A supply of 20(S) camptothecin is obtained from Sigma Chemicals. The CPT is reacted with succinic anhydride in pyridine for two days. The reaction mixture is quenched in water, and is then extracted. Next, the 20-succinyl ester is removed and purified by recrystallization from an appropriate solvent.

Streptozoticin is then obtained from Sigma Chemicals. The streptozoticin is conjugated to the 20-succinyl ester using morphinol ethyl carbodiimde. The resulting compound is purified using liquid chromatography.

The compound is then tested for activity using the human tumor xenograph models outlined in B. C. Giovanella et al., *Protocols for the Treatment of Human Tumor Xenografts with Camptothecins,* 803 Annals of the New York Academy of Sciences 181 (1996), and Henry S. Friedman et al., *Treatment of Central Nervous System Xenografts with Camptothecins,* 803 Annals of the New York Academy of Sciences 210 (1996).

Example 10

The compound of Example 1 is prepared. This compound is then administered intravenously to a patient suffering from pancreatic cancer over the course of one month. The compound is administered five consecutive days, with a two day rest interval.

The size of the tumor over the course of therapy is monitored non-invasively using antibody labeled Tc-99m. Any reductions in size of the tumor or clinical improvement of the patient are noted.

Example 11

The composition of Example 5 is prepared. This composition is then used to prepare a coated stent, using the general teachings of Berg et al. (U.S. Pat. Nos. 5,464,650). A stenotic lesion is then induced in a conventional animal model, namely a pig artery. The nature and dimensions of the stenotic lesion are then determined using a catheter and an appropriate viewing device. The stent is then deployed at the lesion site, using a conventional stent deployment catheter and balloon. After one week, the pig is sacrificed, and the degree of restenotic growth is determined. This amount of growth is compared against a control animal where the deployed stent is not coated.

What is claimed is:

1. A compound comprising 9-nitro-camptothecin or 9-amino-camptothecin, wherein said compound is covalently conjugated at the 20 position to a lactone ring-protecting moiety selected from the group consisting of polyalkylene oxide, dextran, polyvinyl alcohol, carbohydrate polymer, an antibody, and streptozoticin.

2. The compound of claim 1, wherein the polyalkylene oxide is a polyethylene glycol.

3. A composition comprising the compound of claim 1 together with a pharmaceutical excipient.

4. The composition of claim 1, wherein the polyalkylene oxide is a polyethylene glycol.

5. A kit comprising a container that contains the compound of claim 1.

6. The kit of claim 5, wherein the polyalkylene oxide is a polyethylene glycol.

7. A kit comprising a container that contains the composition of claim 3.

8. An implant for administering at least one compound according to claim 1 comprising an implant structure and at least one compound according to claim 1.

9. The implant of claim 8, where the implant comprises a time-release implant.

10. The implant of claim 8, where the implant comprises a gel or polymer implant.

11. The implant of claim 8, where the implant is coated and the at least one compound is contained in the coating.

12. The implant of claim 8, where the at least one compound is contained within the implant structure.

13. The implant of claim 8, wherein the at least one compound is present in an amount effective to reduce cell proliferation once the implant is deployed.

14. The implant of claim 13, where the cell proliferation that is reduced is restenotic or cancerous.

15. The implant of claim 8, where the implant is biodegradable or is formed in situ.

16. The implant of claim 8, where the implant comprises a stent.

17. A method of treatment comprising inserting an implant into a body wherein the implant comprises the implant of claim 8.

18. The method of claim 17, where the method is used to treat restenosis, various types of cancers, insults to body tissue due to surgery, diseases that produce fibrosis of tissue, repetitive motion disorders, disorders of tissues that are not highly vascularized, and proliferative responses associated with organ transplants.

19. The method of claim 17, where the method is used to treat coronary, carotid, and cerebral restenotic lesions.

20. The method of claim 17, where the method is used to treat gliomas, other central nervous system tumors, tumors at localized sites including inoperable tumors, tumors where localized treatment of tumors would be beneficial, and solid tumors.

21. The method of claim 17, where the method is used to treat cell proliferation associated with joint surgery, bowel surgery, and cheloid scarring.

22. The method of claim 17, where the method is used to treat emphysema.

23. The method of claim 17, where the method is used to treat carpal tunnel syndrome.

24. The method of claim 17, where the method is used to treat disorders of tissues that are not highly vascularized.

25. The method of claim 24, where the method is used to treat proliferative responses occurring as a result of transplantation of the heart, lung, liver, kidney, and other body organs or organ systems.

26. The method of claim 17, where the method is used to treat proliferative responses contributing to potential organ rejections or associated complications.

27. A kit comprising an implant and a mechanism capable of inserting the implant into a body, wherein the implant comprises the implant of claim 8.

28. The kit of claim 27, wherein the mechanism is an intraluminal catheter.

29. The kit of claim 27, where the implant comprises a stent.

30. A method of treatment comprising inserting a stent into a body, wherein the stent comprises at least one compound as claimed in claim 1.

31. A kit comprising a stent and a mechanism capable of introducing the stent into a body, wherein the stent comprises at least one compound as claimed in claim 1.

32. An apparatus comprising a container adaptable for connection to an intraluminal catheter, wherein the container contains at least one compound as claimed in claim 1.

33. A method of treating a cell proliferation disease in a host, comprising administering to the host an amount of the compound of claim 1 effective to treat the cell proliferation disease.

34. A method of treatment comprising administering at least one compound as claimed in claim 1 through an intraluminal catheter.

35. A kit comprising a container adaptable for connection to an intraluminal catheter, wherein the container contains at least one compound as claimed in claim 1.

36. A method of treatment comprising administering the compound of claim 1 in a local fashion.

* * * * *